United States Patent

Rühl et al.

[11] Patent Number: 5,641,881
[45] Date of Patent: Jun. 24, 1997

[54] PREPARATION OF N-ALKENYLCARBOXAMIDES

[75] Inventors: Thomas Rühl, Frankenthal; Jochem Henkelmann, Mannheim; Marc Heider, Neustadt, all of Germany

[73] Assignee: BASF Aktiengesellschaft, Ludwigshafen, Germany

[21] Appl. No.: 513,628

[22] Filed: Aug. 10, 1995

[30] Foreign Application Priority Data

Aug. 19, 1994 [EP] European Pat. Off. ............. 94113003

[51] Int. Cl.⁶ .................... C07D 201/08; C07D 207/267; C07C 233/06; C07C 235/36
[52] U.S. Cl. .................. 540/533; 548/552; 548/554; 546/243; 564/215; 564/187; 564/134; 564/135
[58] Field of Search .................... 548/552, 554; 546/243; 540/533; 564/215, 187, 134, 135

[56] References Cited

U.S. PATENT DOCUMENTS

| | | |
|---|---|---|
| 3,424,791 | 1/1969 | Kurtz et al. |
| 3,914,304 | 10/1975 | Schnabel et al. |
| 4,675,442 | 6/1987 | Besecke et al. ............ 564/135 |
| 5,155,253 | 10/1992 | Murray ................... 560/225 |

FOREIGN PATENT DOCUMENTS

| | | |
|---|---|---|
| 1228246 | 11/1966 | Germany. |
| 1245939 | 8/1967 | Germany. |
| 2336977 | 2/1975 | Germany. |
| 2725379 | 12/1978 | Germany. |
| 3237309 | 4/1984 | Germany. |

OTHER PUBLICATIONS

Bayer et al. "Homogenous Catalytic Vinylation of Cyclid Imides and Lactams for the synthesis of N-Vinyl Monomers", Angew Chem., vol. 18 (7), pp. 533–534. 1979.
JP 70/5027 Chem. Abstract Jan. 1970.

*Primary Examiner*—José G. Dees
*Assistant Examiner*—Lily Ledynh
*Attorney, Agent, or Firm*—Keil & Weinkauf

[57] ABSTRACT

Preparation of N-alkenylcarboxamides of the general formula I

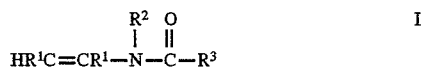

where at least one of the radicals $R^1$ is hydrogen and the second radical $R^1$ is hydrogen or a $C_1$–$C_4$-alkyl group, the radical $R^2$ is an aliphatic, cycloaliphatic, araliphatic or aromatic radical which can be bonded to the radical $R^3$ to give a 3- to 10-membered bridge member, and the radical $R^3$ is hydrogen or an aliphatic, cycloaliphatic or aromatic radical, from an alkenyl carboxylate of the general formula II

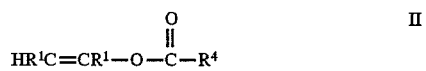

where $R^1$ has the meanings indicated above and $R^4$ is hydrogen or an aliphatic, cycloaliphatic or aromatic radical, and a carboxamide of the general formula III

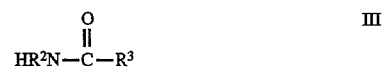

where the radicals $R^2$ and $R^3$ have the meanings indicated above, by reacting the starting compounds in the presence of a base is described.

9 Claims, No Drawings

PREPARATION OF N-ALKENYLCARBOXAMIDES

The present invention relates to a novel process for preparing N-alkenylcarboxamides of the general formula I

where at least one of the radicals $R^1$ is hydrogen and the second radical $R^1$ is hydrogen or a $C_1$–$C_4$-alkyl group, the radical $R^2$ is an aliphatic, cycloaliphatic, araliphatic or aromatic radical which can be bonded to the radical $R^3$ to give a 3- to 10-membered bridge member, and the radical $R^3$ is hydrogen or an aliphatic, cycloaliphatic or aromatic radical, from an alkenyl carboxylate of the general formula II

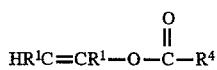

where $R^1$ has the meanings indicated above and $R^4$ is hydrogen or an aliphatic, cycloaliphatic or aromatic radical, and a carboxamide of the general formula III

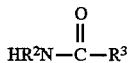

where the radicals $R^2$ and $R^3$ have the meanings indicated above.

The products of the formula I are sought-after intermediates. N-Alkenylcarboxamides can be polymerized in a known manner and then converted into the corresponding polyvinylamines by hydrolysis. These polymers, in particular polyvinylpyrrolidone, are used, for example, as washing aids, as auxiliaries in cosmetic and medicinal ointments, and for the stabilization and clarifying filtration of beers and fruit juices.

Reppe et al. describe the preparation of N-vinylcarboxamides by reaction of carboxamides with acetylene under pressure in the presence of bases (Liebigs Ann. Chem., 601 (1956) 82; DE-A 12 45 939). Working with acetylene requires a large industrial outlay.

DE-A 23 36 977, DE-A 12 28 246 and DE-A 32 37 309 relate to the preparation of substituted N-alkylamides as precursors for N-vinylamides.

These processes for preparing vinylamides are two-stage and require a thermal elimination step. They are thus relatively complicated technically and on account of losses of valuable product at the necessary high reaction temperatures lead only to unsatisfactory total yields.

JP-A 72/20011 describes a process for preparing N-vinylpyrrolidone and N-vinylcaprolactam by vinylation of the lactams with a vinyl ester in the presence of an acid and of a mercury salt. Apart from the use of mercury compounds, which is undesirable for toxicological reasons, the presence of acids always leads to a partial polymerization of the product, which is reflected in an unsatisfactory total yield.

DE-A 27 25 379 relates to a process for preparing N-alkenyl compounds from alkenyl esters and N-substituted carboxamides in the presence of metals of the platinum group, in particular palladium, as catalyst. In industrial processes, reduction of the catalyst occurs in this process, so it is necessary to make up the expensive noble metal compounds.

It is therefore an object of the present invention to provide a process which avoids said disadvantages of known processes.

We have found that this object is achieved by the process for preparing N-alkenylcarboxamides of the formula I defined above, which comprises reacting the starting compounds in the presence of a base.

The reaction equation below illustrates the claimed process as exemplified by the preparation of N-vinylpyrrolidone from vinyl formate and pyrrolidone in the presence of triethylamine (Et=ethyl):

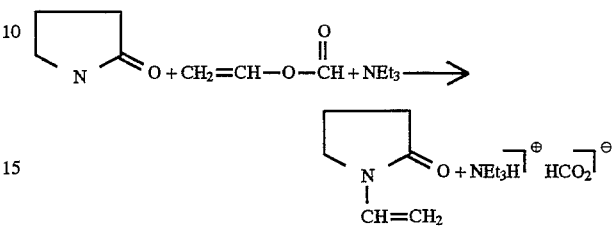

In the process according to the invention, a vinyl group is formally transferred from a carboxylic acid vinyl ester of the formula II to a carboxamide of the formula III.

The vinyl group of the esters of the formula II can carry a $C_1$–$C_4$-alkyl radical such as methyl, ethyl, n-propyl, isopropyl or n-butyl, but compounds are preferred where the radicals $R^1$ are hydrogen. The radical $R^4$ in the esters of the formula II is an aliphatic radical such as an alkyl or alkenyl group, which preferably carries 1 to 40 carbon atoms and can be straight-chain or branched. Particularly preferred radicals are $C_1$–$C_{20}$-alkyl groups such as methyl, ethyl, n-propyl, n-butyl, tert-butyl, neodecyl and stearyl. $R^4$ may furthermore be a cycloaliphatic radical, preferably having 4–7 carbon atoms, eg. cyclopentyl or cyclohexyl. Aromatic radicals such as phenyl and naphthyl are also suitable, it being possible for these to carry substituents which are inert under the reaction conditions, such as halogen, alkoxy and alkyl. Particularly preferably, $R^4$ is additionally hydrogen.

Starting compounds of the formula II which may be mentioned are vinyl formate, vinyl acetate, vinyl propionate, vinyl stearate, vinyl pivalate and 4-tert-butylbenzylvinyl esters.

The compounds of the formula II are commercially available or can be prepared by known methods, for example by addition of carboxylic acids to acetylene or by acetoxylation of ethylene (Weissermel and Arpe, Industrielle Organische Chemie [Industrial Organic Chemistry], 2nd Edition, 1978, Verlag Chemie, p. 217 ff.).

The radical $R^2$ in the carboxamides of the formula III is an aliphatic radical such as an alkyl group, which preferably carries 1 to 10 carbon atoms and is preferably straight-chain or branched. Particularly preferred radicals are $C_1$–$C_4$-alkyl groups such as methyl, ethyl, n-propyl and n-butyl.

$R^2$ can also be a cycloaliphatic radical such as cyclohexyl, an aromatic radical such as phenyl or an araliphatic radical such as benzyl. The radical $R^2$ with the radical $R^3$ can furthermore form a 3- to 10-membered bridge member, of which 3- to 7-membered alkylene bridge members are preferred.

For the radical $R^3$ of the amides of the formula III, what has been said above for the radical $R^4$ applies in a similar manner. Starting compounds which may be mentioned are: pyrrolidone, caprolactam, piperidone, N-methylacetamide, N-phenylacetamide and N-methylbenzoylamide.

These compounds too are commercially available or obtainable by known methods, eg. by reaction of carboxylic acids and primary amines with elimination of water.

Preferred products are N-vinylpyrrolidone and N-vinylcaprolactam.

The starting compounds are reacted in the presence of a base, preferably of a Bronsted base. Both inorganic and organic bases are suitable for this purpose. The bases are specifically carbonates and hydrogencarbonates of the alkali metals and alkaline earth metals, such as sodium carbonate, potassium carbonate and sodium hydrogencarbonates, quaternary ammonium carbonates such as tetramethylammonium carbonate, amides such as alkali metal amides, for example sodium amide and potassium amide, hydroxides such as alkali metal hydroxides, for example lithium hydroxide, sodium hydroxide and potassium hydroxide, alkali metal carboxylates such as sodium acetate, alkoxides such as alkali metal alkoxides, for example sodium methoxide, sodium ethoxide, potasl sium methoxide and potassium tert-butoxide. Potassium hydroxide can also be used together with crown ethers such as 18-crown-6.

Suitable bases are further amines such as ammonia, primary, secondary and tertiary amines, of which the tertiary amines are preferred. The amines can carry aliphatic or aromatic radicals, for example trialkylamines such as trioctylamine, ethyldiisopropylamine, diethylisopropylamine, dimethylcyclohexylamine, triethylamine, additionally cyclic amines such as 2,2,6,6-tetramethylpiperidine, 1,4-diazabicyclo[2.2.2]octane, 1,8-diazabicyclo[5.4.0]undec-7-ene, amines carrying aliphatic and aromatic radicals, such as 1,8-bis(dimethylamino) naphthalene and 4-dimethylaminopyridine, and heterocyclic amines such as N-alkylimidazoles and N-arylimidazoles. Amides which are furthermore suitable are those such as dialkylcarboxamides, eg. dibutylformamide. The process according to the invention can also be carried out in the presence of basic ion exchangers, which as a rule consist of sulfonated styrene/divinylbenzene copolymers such as Amberlite®, Lewatit® and Puralit®, and in the presence of basic zeolites such as hydrotalcite.

Per equivalent of amide of the formula III, from 0.1 to 10, preferably 1 to 1.2 equivalents, of the ester of the formula II can be employed.

The amount of base can be from 0.1 to 3 equivalents, preferably 0.2 to 1 equivalent, per equivalent of amide of the formula III.

Although the reaction is preferably carried out without solvent, it is possible, however, to add a solvent, eg. aprotic solvents such as ethers, eg. tetrahydrofuran, aromatic hydrocarbons such as toluene and xylene, ketones such as acetone, furthermore acetonitrile, hexamethylphosphoramide, sulfolane, dimethyl sulfoxide, ureas such as N,N'-dimethylethyleneurea, N,N'-dimethylpropyleneurea and tetrabutylurea. The amount is in general from 10 to 30% by weight, based on the total mixture.

As a rule, the reaction temperature is from 0° to 150° C., preferably 20° to 80° C. The reaction is preferably carried out at normal pressure, but it is also possible to work at a reaction pressure from 0.01 to 10 bar.

The reaction can be carried out continuously or batchwise. Thus the starting compounds and the base can be added to a stirring vessel and reacted therein, the sequence of addition of the individual components having no discernible effect on the reaction. It is also possible to react the starting compounds and the base in a tubular reactor in a trickle- or liquid-phase process. It has proven advantageous to perform the reaction in a jet tube reactor.

As a rule, the reaction is complete after 5 minutes to 8 hours.

The reaction mixture thus obtained can be worked up in a manner known per se. In general, the product is removed by distillation. The distillation bottom can be treated to liberate the organic bases from the salt formed in the reaction using alkali metal hydroxide solutions such as sodium hydroxide solution. The admixed bases can then be isolated by extraction or distillation. If easily volatile salt-like compounds such as formates of tertiary ammonium compounds are formed in the reaction according to the invention, these can also be worked up by distillation and converted into the corresponding amines. The bases separated off in each case can be fed back into the reaction.

The process according to the invention allows the one-stage preparation of N-alkenylamides from easily accessible precursors. The reaction can be carried out in a technically simple manner and proceeds under mild reaction temperatures. It furthermore leads to a high yield of the products.

EXAMPLES

General reaction procedure a mol of an ester of the formula II, b mol of an amide of the formula III and c mol of base were reacted at x °C. and 1 bar to give the product I. The course of the reaction was monitored by gas chromatography.

The yield was determined by gas chromatography.

The following table indicates details of the reaction:

TABLE

| Example | Ester II | a [mol] | Amide III | b [mol] | Base | c [mol] | X [°C.] | I | Yield [%] |
|---|---|---|---|---|---|---|---|---|---|
| 1 | Vinyl formate | 0.36 | Pyrrolidone | 0.30 | Triethylamine | 0.30 | 50 | N-Vinylpyrrolidone | 85 |
| 2 | Vinyl acetate | 0.30 | Pyrrolidone | 0.30 | DMAP | 0.15 | 60 | N-Vinylpyrrolidone | 92 |
| 3 | Vinyl acetate | 0.30 | N-Methyl-acetamide | 0.30 | DMAP | 0.15 | 60 | N-Vinyl-N-methyl-acetamide | 89 |
| 4 | Vinyl formate | 0.50 | Caprolactam | 0.50 | Dimethylcyclo-hexylamine | 0.50 | 60 | N-Vinylcaprolactam | 87 |
| 5 | Vinyl propionate | 0.30 | Valerolactam | 0.30 | DMAP | 0.30 | 70 | N-Vinylpiperidone | 78 |
| 6 | Vinyl formate | 0.35 | N-Methyl-benzamide | 0.30 | 1,4-Diazabicyclo-[2.2.2]octane | 0.30 | 50 | N-Methyl-N-vinyl benzamide | 75 |
| 7 | Vinyl formate | 0.50 | N-Phenyl-acetamide | 0.50 | Triethylamine | 0.30 | 55 | N-Phenyl-N-vinyl-acetamide | 91 |

We claim:

1. A process for preparing N-alkenylcarboxamides of the general formula I

where at least one of the radicals $R^1$ is hydrogen and the second radical $R^1$ is hydrogen or a $C_1$-$C_4$-alkyl group, the radical $R^2$ is an aliphatic, cycloaliphatic, araliphatic or aromatic radical which can be bonded to the radical $R^3$ to give a 3- to 10-membered bridge member, and the radical $R^3$ is hydrogen or an aliphatic, cycloaliphatic or aromatic radical, from an alkenyl carboxylate of the general formula II

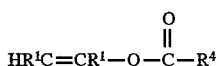
II where $R^1$ has the meanings indicated above and $R^4$ is hydrogen or an aliphatic, cycloaliphatic or aromatic radical, and a carboxamide of the general formula III

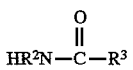
III where the radicals $R^2$ and $R^3$ have the meanings indicated above, which comprises reacting the starting compounds in the presence of a base.

2. A process as claimed in claim 1, wherein the radicals $R^1$ are hydrogen.

3. A process as claimed in claim 1, wherein the radical $R^2$ is a $C_1$–$C_{20}$-alkyl group or, with the radical $R^3$, forms a 3- to 7-membered alkylene bridge member.

4. A process as claimed in claim 1, wherein N-vinylpyrrolidone or N-vinylcaprolactam is prepared.

5. A process as claimed in claim 1, wherein the reaction is performed without solvent.

6. A process as claimed in claim 1, wherein from 0.2 to 1 equivalent of base are used per equivalent of amide of the formula III.

7. A process as claimed in claim 1, wherein the reaction is performed at 20° to 80° C.

8. A process as claimed in claim 1, wherein the base used is a tertiary amine.

9. A process as claimed in claim 1, wherein the base employed is sodium methoxide, potassium tert-butoxide or potassium carbonate.

* * * * *